United States Patent
Prasad (10) Patent No.: US 11,938,152 B2
(45) Date of Patent: Mar. 26, 2024

(54) HIGH-DOSE ANTIOXIDANTS IN CANCER TREATMENT

(71) Applicant: Kedar N Prasad, San Rafael, CA (US)

(72) Inventor: Kedar N Prasad, San Rafael, CA (US)

( * ) Notice: Subject to any disclaimer, the term of this patent is extended or adjusted under 35 U.S.C. 154(b) by 0 days.

(21) Appl. No.: 16/987,008

(22) Filed: Aug. 6, 2020

(65) Prior Publication Data

US 2022/0047625 A1    Feb. 17, 2022

(51) Int. Cl.

| | |
|---|---|
| A61K 33/30 | (2006.01) |
| A61K 9/00 | (2006.01) |
| A61K 31/05 | (2006.01) |
| A61K 31/07 | (2006.01) |
| A61K 31/12 | (2006.01) |
| A61K 31/122 | (2006.01) |
| A61K 31/197 | (2006.01) |
| A61K 31/198 | (2006.01) |
| A61K 31/352 | (2006.01) |
| A61K 31/355 | (2006.01) |
| A61K 31/375 | (2006.01) |
| A61K 31/385 | (2006.01) |
| A61K 31/4415 | (2006.01) |
| A61K 31/455 | (2006.01) |
| A61K 31/51 | (2006.01) |
| A61K 31/519 | (2006.01) |
| A61K 31/525 | (2006.01) |
| A61K 31/593 | (2006.01) |
| A61K 31/714 | (2006.01) |
| A61P 35/00 | (2006.01) |

(52) U.S. Cl.
CPC ............ *A61K 33/30* (2013.01); *A61K 9/0095* (2013.01); *A61K 31/05* (2013.01); *A61K 31/07* (2013.01); *A61K 31/12* (2013.01); *A61K 31/122* (2013.01); *A61K 31/197* (2013.01); *A61K 31/198* (2013.01); *A61K 31/352* (2013.01); *A61K 31/355* (2013.01); *A61K 31/375* (2013.01); *A61K 31/385* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/593* (2013.01); *A61K 31/714* (2013.01); *A61P 35/00* (2018.01)

(58) Field of Classification Search
None
See application file for complete search history.

(56) References Cited

U.S. PATENT DOCUMENTS

| | | |
|---|---|---|
| 9,795,632 B2 | 10/2017 | Perricone |
| 9,849,160 B2 | 12/2017 | Perricone |
| 9,895,323 B2 | 2/2018 | Levy et al. |
| 9,895,357 B2 | 2/2018 | Zemel et al. |
| 9,896,731 B2 | 2/2018 | Narain et al. |
| 9,907,828 B2 | 3/2018 | Janssen-Heininger et al. |
| 9,957,506 B2 | 5/2018 | Cubillos-Ruiz et al. |
| 10,016,392 B2 | 7/2018 | Nezami |
| 10,034,898 B2 | 7/2018 | Perricone |
| 10,111,913 B2 | 10/2018 | Kovarik |
| 10,143,669 B2 | 12/2018 | Feitelson |
| 10,155,048 B2 | 12/2018 | Parricone |
| 10,314,865 B2 | 1/2019 | Kovarik et al. |
| 10,314,866 B2 | 1/2019 | Kovarik |
| 10,195,164 B2 | 2/2019 | Devi |
| 10,201,583 B2 | 2/2019 | Fast et al. |
| 10,220,046 B2 | 3/2019 | Schwendeman et al. |
| 10,231,941 B2 | 3/2019 | Feitelson |
| 10,245,294 B2 | 4/2019 | Ball et al. |
| 10,258,778 B2 | 4/2019 | DiPierro et al. |
| 10,285,971 B2 | 5/2019 | Bromley |
| 10,286,070 B2 | 5/2019 | Joercyk et al. |
| 10,449,211 B2 | 10/2019 | Katibah et al. |
| 10,450,566 B2 | 10/2019 | Cubillos-Ruiz et al. |
| 10,471,034 B2 | 11/2019 | Hamill et al. |
| 10,473,340 B2 | 11/2019 | Hecht et al. |
| 10,478,447 B2 | 11/2019 | Phillips et al. |
| 10,478,461 B2 | 11/2019 | Gammelsaeter et al. |
| 10,493,043 B2 | 12/2019 | Kin et al. |
| 10,501,426 B1 | 12/2019 | Mabkhot et al. |
| 10,517,322 B1 | 12/2019 | Lee |
| 10,519,241 B2 | 12/2019 | Raum et al. |
| 10,519,504 B2 | 12/2019 | Narain et al. |
| 10,526,016 B2 | 1/2020 | Kuang et al. |
| 10,532,202 B2 | 1/2020 | Skiba et al. |
| 10,548,876 B2 | 2/2020 | Garner et al. |
| 10,550,431 B2 | 2/2020 | Rahme et al. |
| 10,555,976 B2 | 2/2020 | Kovarik |
| 10,588,974 B2 | 3/2020 | Lerone-Bay et al. |
| 2003/0147996 A1* | 8/2003 | Prasad .................. A61K 45/06 426/74 |
| 2017/0209405 A1* | 7/2017 | Jalbout ................ A61K 31/385 |
| 2018/0008573 A1* | 1/2018 | Brown ................ A61K 31/047 |

* cited by examiner

*Primary Examiner* — Duane Smith
(74) *Attorney, Agent, or Firm* — Dan De La Rosa (57) ABSTRACT

This invention proposes that a mixture of high doses of multiple antioxidants in combination with therapeutic agents may improve the management of cancer without toxicity.

41 Claims, 11 Drawing Sheets

FIGURE 1:

TABLE 1:

Range of Daily High-Dose Antioxidants Formula For Cancer Treatment

| Type of vitamins | Dose-range |
|---|---|
| Vitamin A (as vitamin A palmitate) | 6,000-25,000 IU |
| Vitamin C (as calcium ascorbate) | 5,000-20,000 mg |
| Vitamin D3 (cholecalciferol) | 3,000 IU- 12,000 IU |
| Vitamin E (as d-alpha-tocopheryl succinate) | 1,000-3,000 IU |
| R-alpha-lipoic acid | 800-1,800 mg |
| Coenzyme Q10 | 800 -2,000 mg |
| Quercetin | 800-2,000 mg |
| Curcumin | 800-2,000 mg |
| Resveratrol | 800-2,000 mg |
| Vitamin B1 (thiamine phosphate) | 6-12 mg |
| Vitamin B2 (riboflavin) | 6-12 mg |
| Vitamin B3 (nicotinamide riboside) | 6-18 mg |
| Vitamin B5 (pantothenic acid) | 6-18 mg |
| Vitamin B6 (as pyrodoxin chloride) | 6-18 mg |
| Vitamin B9 (as methylfolate) | 400-1,200 mcg |
| Vitamin B12 (methylcobalamine | 8-50 mcg |
| Selenomethinine | 50-300 mcg |
| Zinc glycinate | 10-40 mg |

FIGURE 2:

TABLE 2:

Daily High-Dose Antioxidants Formula for Cancer Patients

| | |
|---|---|
| Vitamin A (as retinyl palmitate) | 10,000 IU |
| Vitamin C (as calcium ascorbate) | 10,000 mg |
| Vitamin D3 (as cholecalciferol) | 6,000 IU or 150 mcg |
| Vitamin E (as d-alpha-tocopheryl succinate) | 1,800 IU or 1550 mg |
| R-alpha-lipoic acid | 900 mg |
| Coenzyme Q10 as Quibinol | 900 mg |
| Quercetin | 900 mg |
| Curcumin | 1200 mg |
| Resveratrol | 1200 mg |
| Vitamin B1 (thamine phosphate) | 9 mg |
| Vitamin B2 (riboflavin) | 9 mg |
| Vitamin B3 (nicotinamide riboside) | 12 mg |
| Vitamin 5 (pantothenic acid) | 9 mg |
| Vitamin B6 (as pyridoxine chloride) | 9 mg |
| Vitamin B9 (as methylfolate | 600 mcg |
| Vitamin B12 (methylcobalamine) | 10 mcg |
| Selenomethinine | 100 mcg |
| Zinc glycinate | 15 mg |

FIGURE 3:

TABLE 3:

Effects of a mixture of 4 antioxidants on the growth of human melanoma cells in culture (SK-30 cells)

| Treatments | Growth (% of control) |
|---|---|
| Vitamin C (50 μg/ml) | 102 ± 5a |
| Polar Carotenoids (10 μg/ml) | 96 ± 2 |
| Alpha-tocopheryl succinate (10 μg/ml) | 102 ± 3 |
| 13-cis Retinoic acid (7.5 μg/ml) | 103 ± 3 |
| A mixture of 4 antioxidants | 56 ± 3 |
| Vitamin C (100 μg/ml) | 64 ± 3 |
| A mixture of 4 antioxidants with vitamin C 100 μg/ml) | 13 ± 1 |

Cells were plated in tissue culture dishes, and antioxidants were added 24 h later. Fresh growth medium and antioxidants were changed 2 days after treatment and cell number was counted 3 days after treatment, Growth was determined as % of untreated control. Each experiment was repeated 3 times involving 3 samples per treatment group. Data were taken from a previous publication (73).

FIGURE 4:

TABLE 4:

Enhancement of the Effect of Certain Chemotherapeutic Agents by a Mixture of Four Antioxidants on Human Melanoma Cells in Culture

| Treatments | Cell Number (% of Controls) |
| --- | --- |
| Solvent | $101 \pm 4^a$ |
| Cis-platin (1 μg/ml) | $67 \pm 4$ |
| Antioxidant mixture | $56 \pm 3$ |
| Cisplatin + Antioxidant mixture | $38 \pm 2$ |
| Tamoxifen (2 μg/ml) | $81 \pm 3$ |
| Tamoxifen + Antioxidant mixture | $30 \pm 2$ |
| DTIC (100 μg/ml) | $71 \pm 2$ |
| DTIC + Antioxidant mixture | $38 \pm 2$ |

Data were summarized from a previous publication (73).

a = standard error of the mean

Vitamin C, 50 μg/ml; polar carotenoids, 10 μg/ml; alpha-tocopheryl succinate, 10 μg/ml and 13-cis-retinoic acid, 7.5 μg/ml were added simultaneously with chemotherapeutic agents.

DTIC = 5-(3,3-Dimethyl-1-triazeno) imidazole-4-carboxamide

FIGURE 5:

TABLE 5:

Modification of Adriamycin Effect on Human Cervical Cancer Cells (HeLa) and Human Normal Skin Fibroblasts in Culture by d-α-Tocopheryl Succinate

| Treatment | HeLa Cells | Normal fibroblasts |
|---|---|---|
| Solvent Control | 99 ± 2.6* | 104 ± 3.4 |
| Adriamycin (0.1 µg/ml) | 57 ± 6.2 | 77 ± 2.4 |
| α-TS (10 µg/ml) | 99 ± 1.6 | 101 ± 3.7 |
| Adramycin (0.1 µg/ml) Plus α-TS | 20 ± 7.9 | 77 ± 1.7 |
| Adriamycin (0.25 µg/ml) | 14 ± 2.9 | 68 ± 1.0 |
| Adriamycin (0.25 µg/ml) Plus α-TS | 5 ± 0.8 | 62 ± 1.8 |

Cells (20,000) were plated in 24-well chamber and Adriamycin and α-tocopheryl succinate (α-TS) were added one after another at the same time. Drug, α-TS and fresh growth medium were changed at 2 days after treatment and the viability of cells was determined by MTT assay. Growth in experimental groups was expressed % of untreated control. Each experiment was repeated at least twice, and each value represents an average of 6-9 samples ± SEM (39). .

FIGURE 6:

TABLE 6:

Effect of Alpha Tocopheryl Succinate (α-TS) on Hyperthermia-Induced Growth Inhibition in Neuroblastoma Cells in Culture

| Treatments | Cell Number (% of Controls) |
| --- | --- |
| Solvent (ethanol 0.25%) + Sodium Succinate (5 μg/ml) | 102 ± 3 |
| α-TS (5 μg /ml) | 50 ± 3 |
| 43°C (20 min) | 43 ± 1 |
| α-TS + 43°C | 9 ± 1 |
| 41°C (45 min) | 56 ± 3 |
| α-TS + 41°C | 21 ± 2 |
| 40°C (8 hr) | 55 ± 2 |
| α-TS + 40°C | 30 ± 2 |

Data were summarized from a previous publication Values are mean ± SEM (78)

FIGURE 7:

Figure 7. Melanoma cells ($10^5$) were plated in tissue culture dishes (60 mm), and *d*-alpah-tocopheryl succinate (α-TS) and sodium succinate plus ethanol was added to separate cultures 24 h after plating. Vitamin E and medium were changed at 2 and 3 d after treatment. Photomicrographs were taken 4 d after treatment. Control cultures showed fibroblastic cells as well as round cells in clumps (1A); cultures treated with ethanol (1%) and sodium succinate (5-6 µg/ml) also exhibited fibroblastic morphology with fewer round cells (1B); α-TS-treated cultures 6 µg/ml (1C), and 8 µg/ml (1D) showed a dramatic change in morphology, Mag. X 300.

FIGURE 8:

Diagrammatic representations of the effects of high doses of antioxidants alone or in combination of therapeutic agents on cancer cells and normal cells

No effect of ←―←―High-Dose Antioxidants →―→―→ No effect on

Therapeutic agents ↓ ↓ normal Cells on normal cells ↓ ↓

↓ ↓

↓ ↓

Blocks glucose uptake     Inhibits glutamine metabolism

↓    ↓ ↓ ↓       ↓

↓    ↓ ↓ ↓       ↓

↓     Growth inhibition of cancer cells    ↓

↓                                               ↓

Enhances the effect of therapeutic agents on cancer cells

FIGURE 9:

Figure 9. Effect of alpha-tocopheryl succinate on the level of gamma-radiation-induced chromosomal damage in human cervical cancer (HeLa cells), ovarian carcinoma cell line (OVG1 and SKOV3) and human normal fibroblasts (GM2149), HF19, and AG1522). Alpha-tocopheryl succinate treatment increased chromosomal damage as well enhanced radiation-induced chromosomal damage in all 3 cancer cell lines but not in normal cell line.

FIGURE 10:

Figure 10. Neurobalstoma cells were plated in tissue culture dishes (60 mm), and 5-fluorouracil (5-FU, 0.08 µg/ml together with various concentration of sodium ascorbate were added 24 hours after plating. Fresh medium, 5-FU, and sodium ascorbate changed 2 days after treatment and cells were counted 3 days after treatment. The number of cells in treated groups was expressed as % of untreated controls). Each value is the average of 6-9 samples + Standard deviation.

FIGURE 11:

Figure 11. Neuroblastoma cells (NBP2) were gamma-irradiated 24 after plating in tissue culture dishes. Vitamin E succinate or solvent was added immediately before irradiation. Fresh growth medium, vitamin E succinct, and solvent was changed 2 days after irradiation. Cells were counted 3 days later. The number of cells in treated groups was expressed as % of untreated controls. Each experiment was repeated at least twice involving 3 samples per experiment. The bar at each point is SEM.

HIGH-DOSE ANTIOXIDANTS IN CANCER TREATMENT

FIELD OF THE INVENTION

The field of the invention and its embodiments relate to a composition containing antioxidants, vitamins, phytonutrients, and minerals that is to be administered to cancer patients. The invention maybe administered to cancer patients before, during or after receiving traditional medical treatments for cancer. The invention may also be administered to patients who are not receiving an traditional medical treatments.

BACKGROUND OF THE INVENTION

Problems of current therapies, which include radiation therapy, chemotherapy, and experimental therapies, are severe toxicity during treatment. In some cases toxicity becomes a limiting factor for the continuation of therapy. In addition, some cancer patients become resistant to all cancer therapies.

Survivors of cancer treatment have increased risk of recurrence of primary tumor or development of a new primary tumor as well as non-cancerous diseases.

Problems of current therapies are solved by this invention, high-dose antioxidants kill cancer cells but not normal cells. High-dose antioxidants enhance cell-killing effects of cancer therapeutic agents, while reducing their toxicity. High-dose antioxidants also kill those cancer cells, which have become resistant to all therapies, and thereby, may prolong survival time with good quality of life.

High doses of antioxidants inhibit the growth of cancer cells and enhance the growth-inhibitory effects of standard and experimental therapy on cancer cells but not on normal cells. Cancer cells utilize glucose to generate very small amounts of ATP by an inefficient process glycolysis. Therefore, cancer cells require a lot of glucose to generate sufficient energy for survival and growth. In contrast, normal cells use less glucose to produce a lot of ATP by tricarboxylic acid cycle, a very efficient process. Glutamine, which is referred to as a conditional amino acid, is produced in normal cells only under stress. Since cancer cells are under metabolic stress, they require glutamine for their survival and growth. Cancer cells utilize glutamine for generating energy as well as vital molecules such as protein and DNA; High doses of antioxidants inhibit the uptake of glucose and metabolism of glutamine, which can create an energy crisis and reduced levels of vital molecules. These changes activate apoptotic pathway leading to death of cancer cells. Excessive amounts of free radicals are required for rapid growth and metastasis. Cancer cells are protected from oxidative damage by high expression of Nrf2, which increases the levels of glutathione peroxidase that enhances the levels of glutathione, a powerful antioxidant. However, high doses of antioxidants bypass these protective mechanisms by reducing glucose uptake and inhibiting glutamine metabolism. These changes in cancer cells may reduce the rate of proliferation and the risk of metastasis.

The above effects of high-dose antioxidants are due to blocking the uptake of glucose and inhibiting the metabolism of glutamine in cancer cells. These are required for survival and growth of cancer cells.

Cancer survivors who were given high-dose antioxidants may have decreased risk of recurrence of primary tumor, development of a new cancer and non-cancerous diseases.

SUMMARY OF THE INVENTION

Current cancer therapies produce severe toxicity during treatment, and in some cases toxicity become a limiting factor for the continuation of therapies. Some patients become resistant to all cancer therapies. Cancer survivors have increased risk of recurrence of primary tumor, and development of a new cancer and non-cancerous diseases. The invention claimed here solves these problems.

The claimed invention differs from what currently exists. High-dose antioxidants may enhance cell-killing effects of cancer therapeutic agents on cancer cells, while reducing their toxicity.

The claimed invention differs from what currently exists. High-dose antioxidants kill cancer cells, but not normal cells.

Some cancer patients become resistant to all cancer therapies. The claimed invention solves this problem. High-dose antioxidants may kill the drug resistant cancer cells and restored their sensitivity to therapeutic agents.

Cancer cells require high levels of free radicals for their rapid growth and metastasis. High-doses antioxidants bypass their protective mechanisms leading to reduced growth and metastasis of cancer cells. The claimed invention solves this problem.

The above effects of High-dose antioxidants are due to blocking the uptake of glucose and inhibiting the metabolism of glutamine. These nutrients are required for the survival and growth of cancer cells.

Cancer survivors who were given high-dose antioxidants may have decreased risk of recurrence of primary tumor, and development of a new primary tumor and non-cancerous diseases.

In an embodiment, a composition comprising at least one antioxidant, at least one vitamin, at least one phytonutrient, and at least one mineral.

In another embodiment, a composition wherein the antioxidant is selected of a group comprising of R-alpha-lipoic acid, Coenzyme Q10, Vitamin A, Vitamin C, Vitamin E and combinations thereof.

In still another embodiment, a composition wherein the vitamin is selected from a group comprising of Vitamin D3, Vitamin B1, methylfolate Vitamin B2, Vitamin B3, Vitamin B5, Vitamin B6, Vitamin B9, Vitamin B12 and combinations thereof.

In yet another embodiment, a composition wherein the phytonutrient is selected from a group comprising of curcumin, resveratrol, Quercetin and combinations thereof.

In still yet another embodiment, a composition wherein the mineral is selected form a group comprising selenomethanine, zinc glycinate and combinations thereof.

In a further embodiment, a composition wherein the composition comprises from about 1.8 mg to about 20,000 mg of the antioxidant.

In still a further embodiment, a composition wherein the composition comprises from about 8 mcg to about 1800 mcg of the vitamin. In yet a further embodiment, a composition wherein the composition comprises from about 800 mg to about 2,000 mg of the phytonutrient. In still yet a further embodiment, a composition wherein a composition comprises from about 50 mcg to about 40,000 mcg of the mineral.

In another embodiment, a composition having from about 6,000 IU to about 25,000 IU of Vitamin A. In still another embodiment, a composition wherein the Vitamin A is retinyl palmitate.

In yet another embodiment, a composition having from about 5,000 IU to about 20,000 mg of Vitamin C. In still yet another embodiment, a composition wherein the Vitamin C is calcium ascorbate.

In a further embodiment, a composition of claim 3 having from about 3,000 IU to about 12,000 IU of Vitamin D3. In still a further embodiment, a composition wherein the Vitamin D3 is cholecalciferol.

In yet a further embodiment, a composition having from about 1,000 IU to about 3,000 IU of Vitamin E. In still yet a further embodiment, a composition wherein the Vitamin E is d-alpha-tocopheryl succinate.

In another embodiment, a composition having from about 6 mg to about 12 mg of Vitamin B1. In still another embodiment, a composition wherein the Vitamin B1 is thymine phosphate.

In yet another embodiment, a composition having from about 6 mg to about 12 mg of Vitamin B2. In still yet another embodiment, a composition wherein the Vitamin B2 is riboflavin.

In a further embodiment, a composition having from about 6 mg to about 18 mg of Vitamin B3. In still a further embodiment, a composition wherein the Vitamin B3 is nicotinamide riboside.

In yet a further embodiment, a composition having from about 6 mg to about 18 mg of Vitamin B5. In still yet a further embodiment, a composition wherein the Vitamin B5 is pantothenic acid.

In another embodiment, a composition of having from about 6 mg to about 18 mg of Vitamin B6. In still another embodiment, a composition of wherein the Vitamin B6 is pyridoxine chloride.

In yet another embodiment, a composition of having from about 400 mcg to about 1,200 mcg of Vitamin B9. In still yet another embodiment, composition wherein the Vitamin B9 is methylfolate.

In a further embodiment, a composition having from about 8 mcg to about 50 mcg of Vitamin B12. In still a further embodiment, a composition of wherein said Vitamin B12 is methylcobalamine.

In yet a further embodiment, a composition of having from about 800 mg to about 2,000 mg of curcumin.

In still yet a further embodiment, a composition of having from about 800 mg to about 2,000 mg of resveratrol.

In another embodiment, a composition having from about 800 mg to about 2,000 mg of quercetin.

In still another embodiment, a composition having from about 50 mcg to about 300 mcg of selenomethionine.

In still yet another embodiment, a composition having from about 10 mg to about 40 mg of zinc glycinate.

In still yet another embodiment, a composition having from about 800 mg to about 1,800 mg of R-alpha-lipoic acid.

In a further embodiment, a composition having from about 800 mg to about 2,000 mg of Coenzyme Q10.

In still a further embodiment, a composition is to be given cancer patients. In yet a further embodiment, a composition having a total dose to be administered to cancer patients per day. In another embodiment, a composition wherein in said total dose is to be split into three equal parts and administered three times per day to cancer patients. In still another embodiment, a composition is to be administered orally to cancer patients with a meal.

In yet another embodiment, a composition is to be administered for at least one week before standard cancer therapy. In still yet another embodiment, a composition is to be administered for at least one week before experimental cancer therapy.

In a further embodiment, a composition is to be administered orally to cancer patients with cancer therapy. In still a further embodiment, a composition is to be administered orally to cancer patients without cancer therapy.

In yet a further embodiment, a composition that is in a form selected from a group comprising of powder form or liquid form, and combinations thereof.

In still yet a further composition comprising Vitamin A in a range from about 6,000 IU to about 25,000 IU; Vitamin C in a range from about 5,000 mg to 20,000 mg; Vitamin D3 in a range from about 3,000 IU to about 12,000 IU; Vitamin E in a range from about 1,000 IU to about 3,000 IU; R-alpha-lipoic acid in a range from about 800 mg to about 1,800 mg; Coenzyme Q10 in a range from about 800 mg to about 2,000 mg; Quercetin in a range from about 800 mg to about 2,000 mg; Curcumin in a range from about 800 mg to about 2,000 mg; Resveratrol in a range from about 800 mg to about 2,000 mg; Methylfolate in a range from about 400 mcg to about 1,200 mcg; Vitamin B1 in a range from about 6 mg to about 12 mg; Vitamin B2 in a range from about 6 mg to about 12 mg; Vitamin B3 in a range from about 6 mg to about 18 mg; Vitamin B5 in a range from about 6 mg to about 18 mg; Vitamin B6 in a range from about 6 mg to about 18 mg; Vitamin B12 in a range from about 8 mcg to about 50 mcg; Selenomethionine in a range from about 50 mcg to about 300 mcg; and Zinc in a range from about 10 mg to about 40 mg.

The embodiments of the present invention will now be described with reference to the tables and figures. Identical elements in the various figures are identified with the same reference numerals. Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present tables and figures that various modifications and variations can be made thereto.

DETAILED DESCRIPTION OF THE INVENTION

As required, detailed embodiments of the present invention are disclosed herein; however, it is to be understood that the disclosed embodiments are merely exemplary of the invention that may be embodied in various forms. Therefore, specific structural and functional details disclosed herein are not to be interpreted as limiting, but merely as a basis for the claims and as a representative basis for teaching one skilled in the art to variously employ the present invention.

The specific example below will enable the invention to be better understood. However, they are given merely by way of guidance and do not imply any limitation.

The version of the invention discussed here includes high-dose antioxidants reduce growth and enhance growth-inhibitory effects of cancer therapeutic agents on cancer cells, but not on normal cells. Cancer Survivors who were given high-dose antioxidants may have reduced risk of recurrence of primary tumor, and development of cancer and non-cancerous diseases.

High-dose antioxidants mixture contains vitamin A, vitamin C, vitamin E, vitamin D3, natural beta-carotene, curcumin, resveratrol, coenzyme Q10, all B-vitamins minerals selenium and zinc.

Figure 1:
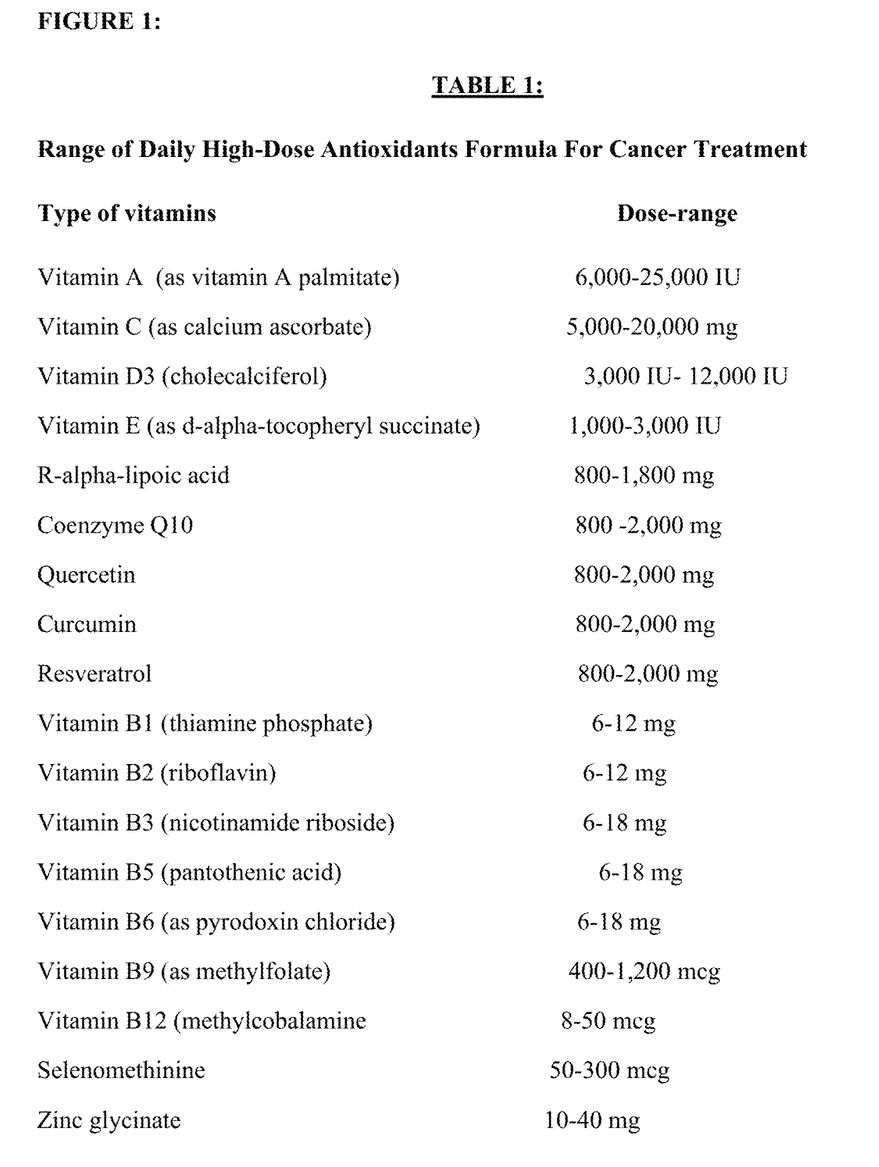
FIG. 1 shows a table showing the ranges of the ingredients for the present invention.
Figure 2:
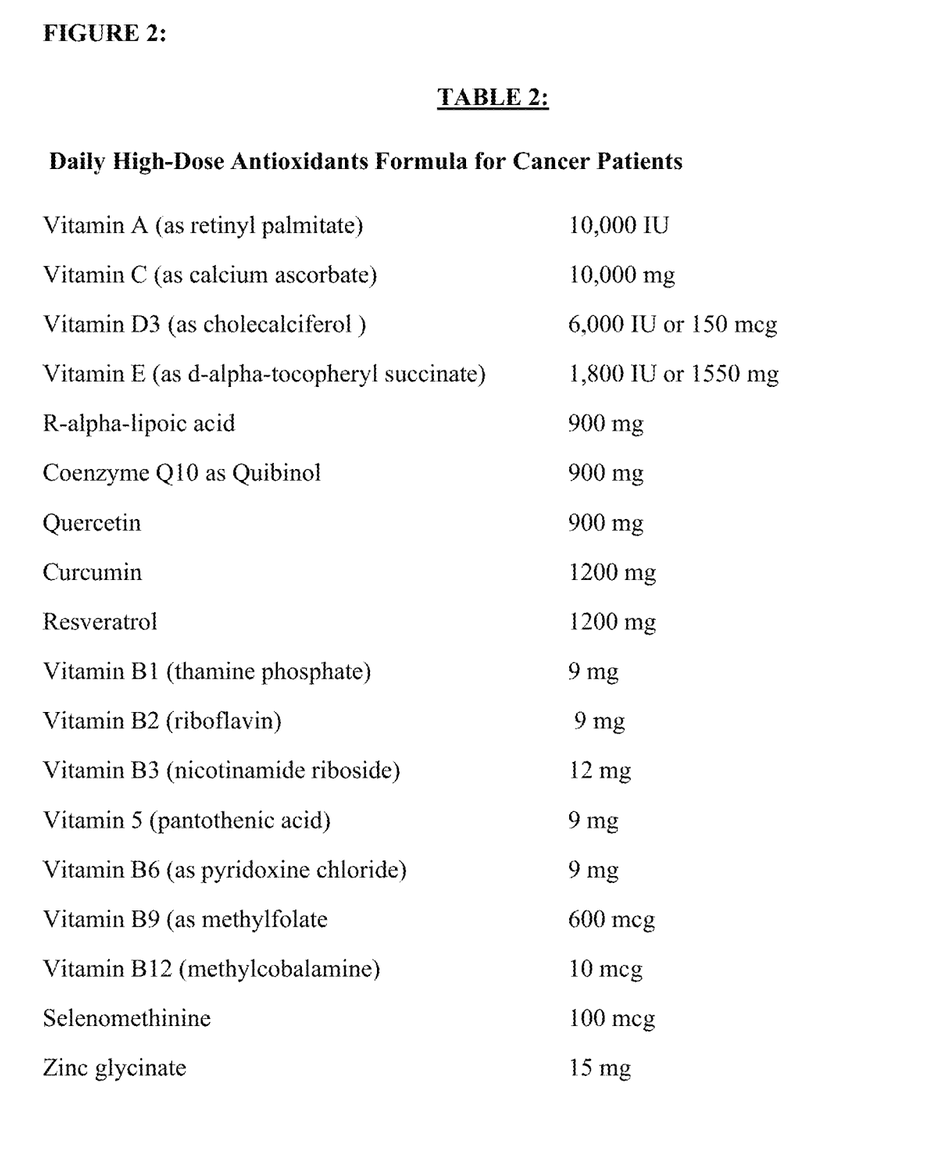
FIG. 2 shows a table of a formulation of the present invention.

Dose range of each antioxidants and other micronutrient of the Formula is presented in Table 1 of FIG. 1. Daily dose of each antioxidant and other micronutrient of the Formula is presented in Table 2 of FIG. 2.

Cancer cells require excess glucose uptake to generate energy by glycolysis, a very inefficient energy-generating pathway, for the survival and growth. Cancer cells also need glutamine metabolism to produce vital molecules for their survival and growth.

High-dose antioxidants blocked the uptake of glucose and inhibit glutamine metabolism, creating an energy crisis and reduction in the levels of vital molecules, which lead to death of cancer cells. By these mechanisms, high-dose antioxidants kill cancer cells but not normal cells, and enhance the growth-inhibitory effects of cancer therapeutic agents on cancer cells, but while protecting normal cells.

Tumor cells require high levels of free radicals for their rapid growth and metastasis. Generally free radicals kill cancer cells. However cancer cells protect themselves against free radicals by permanently inducing high expression of Nrf2, a nuclear transcriptional factor, which when activated by reactive oxygen species (ROS) migrates to the nucleus where it binds with antioxidant response element (ARE) leading to increased production of antioxidant enzymes, such as glutathione peroxidase, superoxide dismutase, and catalase. High expression of glutathione peroxidase in cancer cells protects them from free radical damage by increasing the synthesis of glutathione, a powerful antioxidant. High-dose antioxidants bypass these acquired protective mechanisms in cancer cells and reduce the rate of cell proliferation and the risk of metastasis by blocking glucose uptake and inhibiting glutamate metabolism.

The present invention is based on the inventor's previous original research that high-dose antioxidants kill cancer cells in culture, and they enhance the killing-effects of therapeutic agents on cancer cells, but not on normal cells. Others have reported that high-dose antioxidants block the uptake of glucose and reduce glutamine metabolism, which are required for the survival and growth of cancer cells. These two observations led to the present invention. The data supporting above statements are discussed in this section.

Experience Required for the Invention

Individuals must have published research articles on the effects of high doses of antioxidants on cancer cells and normal cells.

The inventor was the first to demonstrate that a mixture of multiple antioxidants is more effective in reducing the growth of cancer cells than the individual antioxidants. Therefore this invention proposes a mixture of high-dose antioxidants containing multiple dietary and endogenous antioxidants, which include vitamin E in the form of d-alpha-tocopheryl succinate, vitamin A in the form of retinyl palmitate, vitamin C in the form of calcium ascorbate. beta-carotene from the natural sources, vitamin D3, coenzyme Q10 in the form of Quibinol, selenium in the form of selenomethionine, zinc as zinc glycinate, and all B-vitamins. Iron, copper, manganese, and heavy metals are excluded.

All proposed antioxidants, B-vitamins and minerals are necessary for the effectiveness of high-dose antioxidant mixture with or without cancer therapeutic agents in cancer treatment. High-dose antioxidant mixture is prepared in powder form, which can be dissolved in water or juice.

Dissolve powder form of high-dose antioxidant mixture in water or juice. Take orally daily dose divided into 3 doses morning with breakfast, noon with lunch, and evening with dinner. If cancer patients are to receive standard treatment, administer high-dose antioxidant mixture 7 days before the start of standard treatment and continue for the entire treatment period, and 7 days after completion of therapy.

If cancer patients have become unresponsive to all therapies, they are administered orally high-dose antioxidant mixture for two weeks. If the tumor shows some regression, the treatment period can be continued with or without standard cancer therapeutic agents until the patients recovers fully or they become unresponsive to treatments. High-dose antioxidants mixture may also restore the sensitivity of cancer cells to therapeutic agents.

Cancer survivors, who received high-dose antioxidant mixture, may have decreased risk of recurrence of primary tumor, and development of new cancer and non-cancerous diseases.

Several investigations and reviews have shown that high-dose antioxidants inhibit growth of cancer cells without affecting the growth of normal cells in cell culture and animal models (1-7). High doses of antioxidant also enhance the growth-inhibitory effects of therapeutic agents in cancer cells, but they either protect or have no effect in normal cells (1, 8-13). These observations have not drawn any significant attention from cancer researchers or oncologists, because no mechanistic basis of these effects has been proposed. The free radical scavenging function of antioxidants could not explain them.

Studies have shown that excessive uptake of glucose (14, 15) and metabolism of glutamine are required for the survival and growth of cancer cells (16-24). High-dose antioxidants have been reported to block glucose uptake (25-29) and inhibit glutamine metabolism (30-32).

High Doses of Individual Antioxidant Inhibit the Growth of Cancer Cells but not of Normal Cells Vitamin C: Dr. Linus Pauling was the first to demonstrate that vitamin C at high doses inhibits the growth of cancer cells without affecting the growth of normal cells in humans. We demonstrated that vitamin C at a high concentration of killed 100% of murine neuroblastoma (NB) cells in culture. Glutathione, a powerful antioxidant, was more effective than vitamin C in killing NB cells. Growth of murine normal fibroblast was only slightly reduced by the treatment with high doses dose of vitamin C. Vitamin C at high doses inhibited the growth of tumorigenic parotid acinar cells in culture, but had no effect on the growth of non-tumorigenic parotid acinar cells.

Beta-carotene and retinol: Beta-carotene and retinol treatment at high doses induced differentiation in murine NB cells and B-16 murine melanoma cells in culture, respectively.

Figure 7:
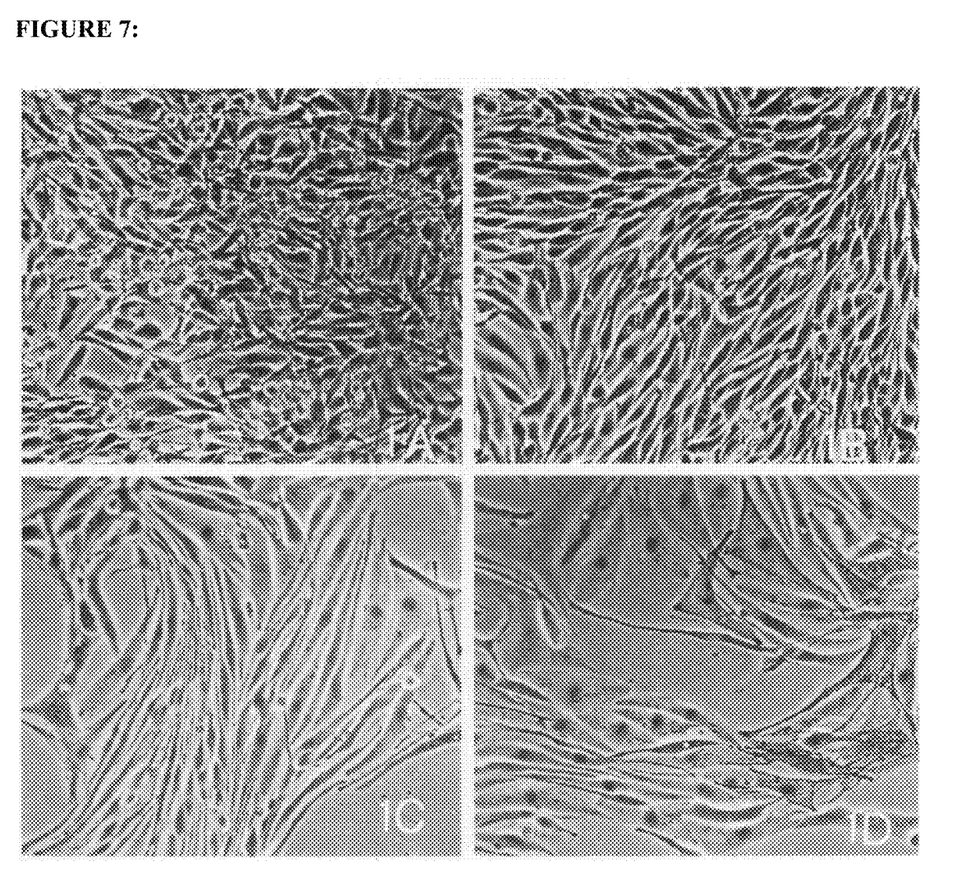
FIG. 7 shows plated tissue treated with d-alpha-tocopheryl.

D-alpha tocopheryl succinate (vitamin E succinate): In 1982, we discovered that vitamin E succinate at high doses induced differentiation and growth inhibition in murine melanoma cells in culture (FIG. 7). Vitamin E succinate at a growth-inhibitory dose reduced the expression of oncogenes c-myc and H-ras. Several studies using other cancer cell lines in culture and in animal models confirmed this observation. Vitamin E succinate treatment of murine neuroblastoma cells at growth inhibitory dose markedly alters the expression of gene profile, which differs from that found at a non-growth-inhibitory dose.

Quercetin: Quercetin treatment induced apoptosis and inhibited the growth of human colon cancer cells overexpressing Cox-2 enzyme (HT29 cells) by generating excessive amounts of reactive oxygen species (ROS). These effects of quercetin are mediated by activating capase-3, increasing the level of cytosolic cytochrome c, and decreasing the levels of phosphorylated AKT and cyclin D1. Quercetin treatment was less effective in HCT 15 cell line expressing reduced level of COX-2 enzyme, and had a minimal effect on normal epithelial cell line (IEC-6).

Resveratrol: Resveratrol treatment reduced the growth of human leiomyoma cells in culture by inhibiting alpha vbeta3, CDKN2, and IGF-1R. It also reduced the level of phosphorylated AKT and increased the expression of pro-apoptotic genes, such as COX-2, P21, and decreased the expression of anti-apoptotic genes such as Bcl2.

Coenzyme Q10: A few clinical studies showed that daily supplementation of coenzyme Q10 390 mg or more may increase the survival of breast cancer patients receiving standard cancer therapy. On the other hand, another clinical study on breast cancer revealed that supplementation with 300 mg coenzyme Q10 did not improve the extent of fatigue or the quality of life.

Curcumin: A few reviews and studies have shown that curcumin, which exhibits antioxidation and ant-inflammatory activities, inhibits the growth and induces apoptosis in various cancer cells in culture by activating the apoptotic signals and attenuating the anti-apoptotic signals. Using cell culture and xenograft models of gastric carcinoma, it was demonstrated that curcumin treatment inhibited growth by inhibiting Wnt/β-Catenin. Curcumin reduced the proliferation of human colon cancer cells in culture by inhibiting the expression of YAP (yes-associated protein regulating cell proliferation).

Figure 8:
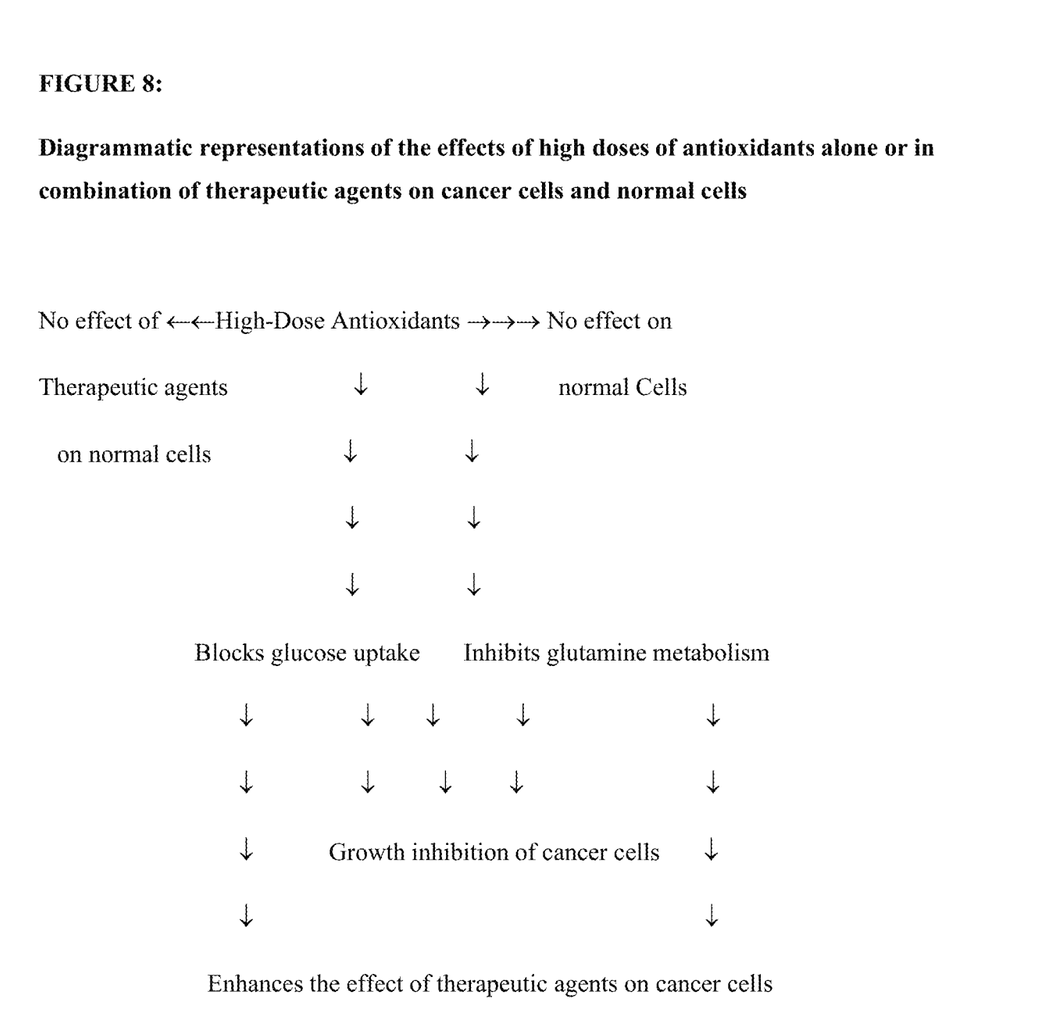
FIG. 8 shows diagrammatic representations of the effects of high doses of antioxidants alone or in combination of therapeutic agents on cancer cells and normal cells.

Diagrammatic representation of the effects of high doses of antioxidants on cancer cells and normal cells is shown in FIG. 8.

Antioxidant Mixture Inhibited the Growth of Cancer Cells but not of Normal Cells Several reviews and studies on the effectiveness of a mixture containing high-dose multiple antioxidants in reducing the growth of cancer cells and enhancing the levels of apoptosis induced by standard and experimental cancer therapeutic agents have been published.

A mixture of micronutrients containing ascorbic acid, quercetin, green tea extract, lysine, and proline reduced growth of human ovarian cells in culture and in athymic mice. The elimination of quercetin the ability of this mixture to inhibit the growth of human neuroblastoma cells in culture and in athymic mice, head and neck squamous cell carcinoma cell line FaDu in culture and in athymic mice, and human leukemic cell line U-937. Another micronutrient mixture containing quercetin, curcumin, resveratrol, green tea extract, and cruciferex inhibited human Faconi anemia head and neck squamous cell carcinoma in culture (OHSU-974 cell line), in athymic mice and in fibrosarcoma HT-180 and melanoma A2058.

Figure 3:
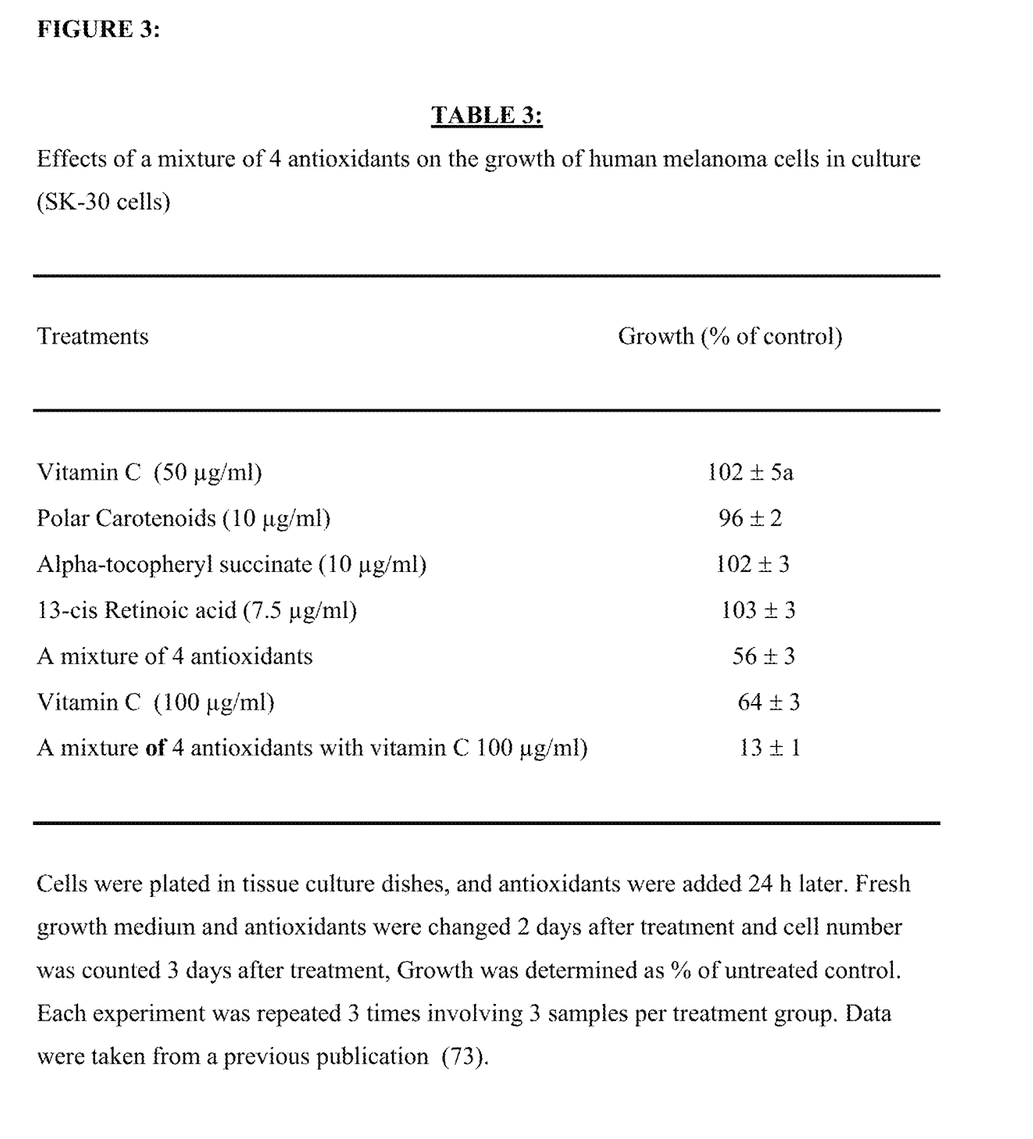
FIG. 3 shows a table with the effects of antioxidants on human melanoma cells.

A mixture of antioxidants containing vitamin C, vitamin E, and beta-carotene enhanced the cytotoxic effects of combined treatment with paclitaxel and carboplatin on human lung squamous cell carcinoma cell line H520. Another mixture of antioxidants containing vitamin C, retinoic acid, polar carotinoids, and d-alpha-tocopheryl succinate reduced the growth of human melanoma cells in culture by about 50% (Table 3 in FIG. 3). It is significant that when any of the above four antioxidants were used individually, they had no effect on the growth of human melanoma cells in culture, but when they were used in combination, they produced about 50% growth inhibition in human melanoma cells in culture. This suggests that antioxidants in the mixture interact with each other to reduce the growth of cancer cells. In addition, increasing the vitamin C dose to growth-inhibitory level in the mixture dramatically reduced the growth of melanoma cells. This suggests that high doses of all four antioxidants might have produced more dramatic inhibition of growth of these cells. The same antioxidant mixture reduced the growth of tumorigenic parotid acinar cells (2HP1G) without significantly affecting the growth of non-tumorigenic parotid acinar cells (2HPC8) in culture.

High Doses of Antioxidants in Combination with Standard Cancer Therapeutic Agents Vitamin A and Beta-carotene: Vitamin A and beta-carotene produced one-year survival in x-irradiated mice with transplanted adenocarcinoma compared to no survival in x-irradiated controls. Beta carotene reduced radiation-induced oral mucositis without interfering with the efficacy of radiation therapy in patients with head and neck cancer.

Figure 10:
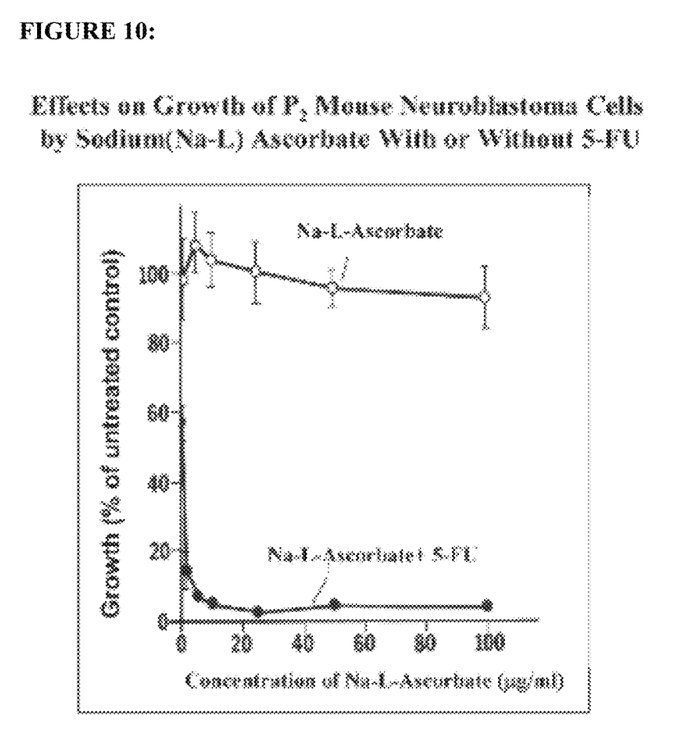
FIG. 10 shows effects of neuroblastoma cells treated with sodium ascorbate.

Vitamin C: As early as in 1979, it was demonstrated that vitamin C as sodium ascorbate enhanced the growth-inhibitory effects of x-radiation and certain chemotherapeutic agents in neuroblastoma cells in culture. For example, vitamin C enhance growth-inhibitory-effect of 5-FU (5-Fluorouracil) in neuroblastoma cells in culture (FIG. 10).

Vitamin C at a daily dose of 1500 mg reduced oxidative stress in patients with differentiated thyroid cancer receiving radioiodine therapy; however, whether or not cancer cells were also protected from oxidative damage of radioiodine therapy was not evaluated. Intravenous administration of high doses of vitamin C as ascorbic acid increased overall survival time in patients receiving combination of gemcitabine and radiation therapy for the management of locally advanced, borderline resectable pancreatic cancer. This study also demonstrated that high doses of ascorbate sensitize the effect of radiation on pancreatic cancer cells but inhibited radiation-induced damage to normal cells.

Figure 5:
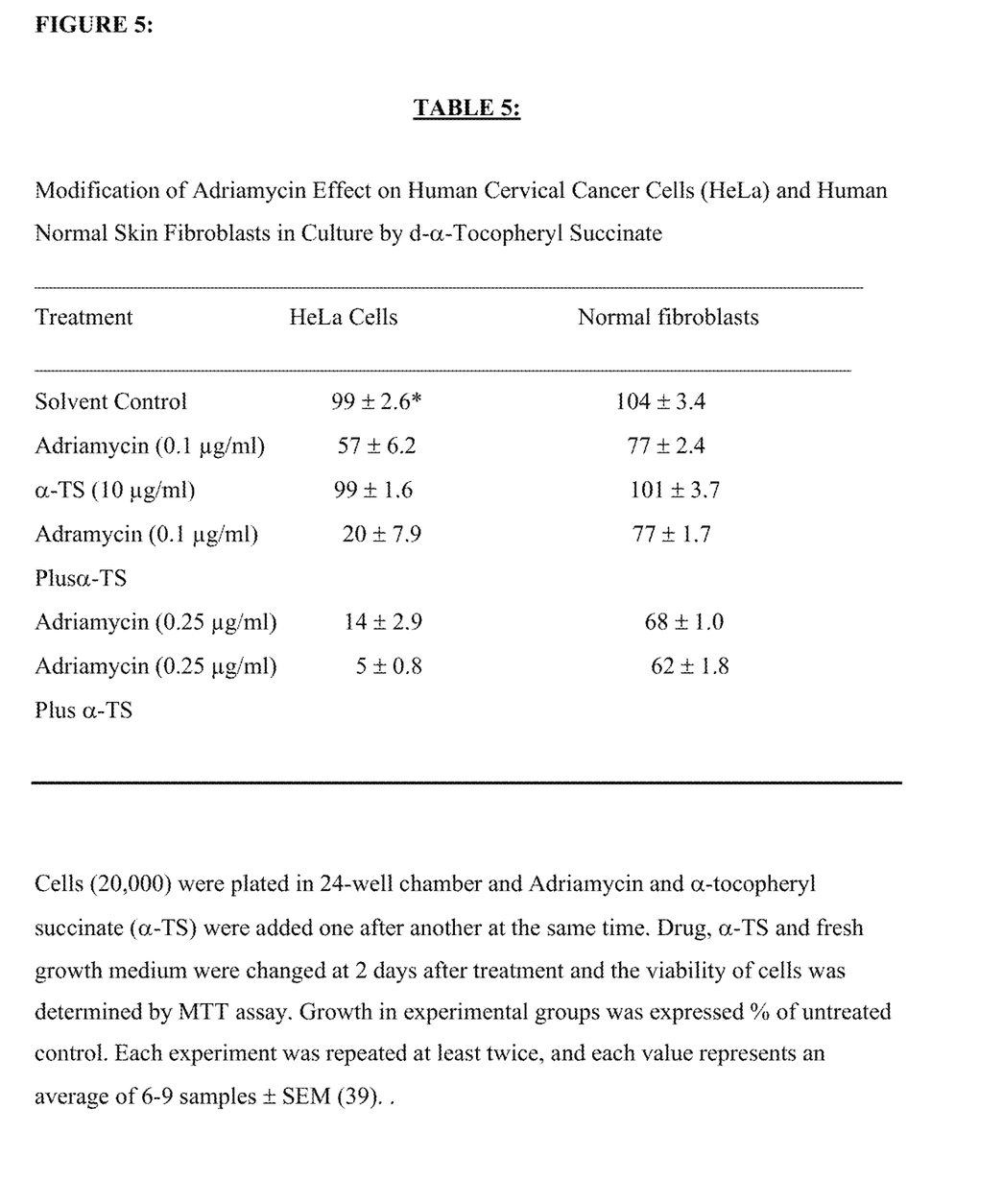
FIG. 5 shows a table with the modification of Adriamycin effect on cancer cells by d-alpha-tocopheryl succinate.
Figure 9:
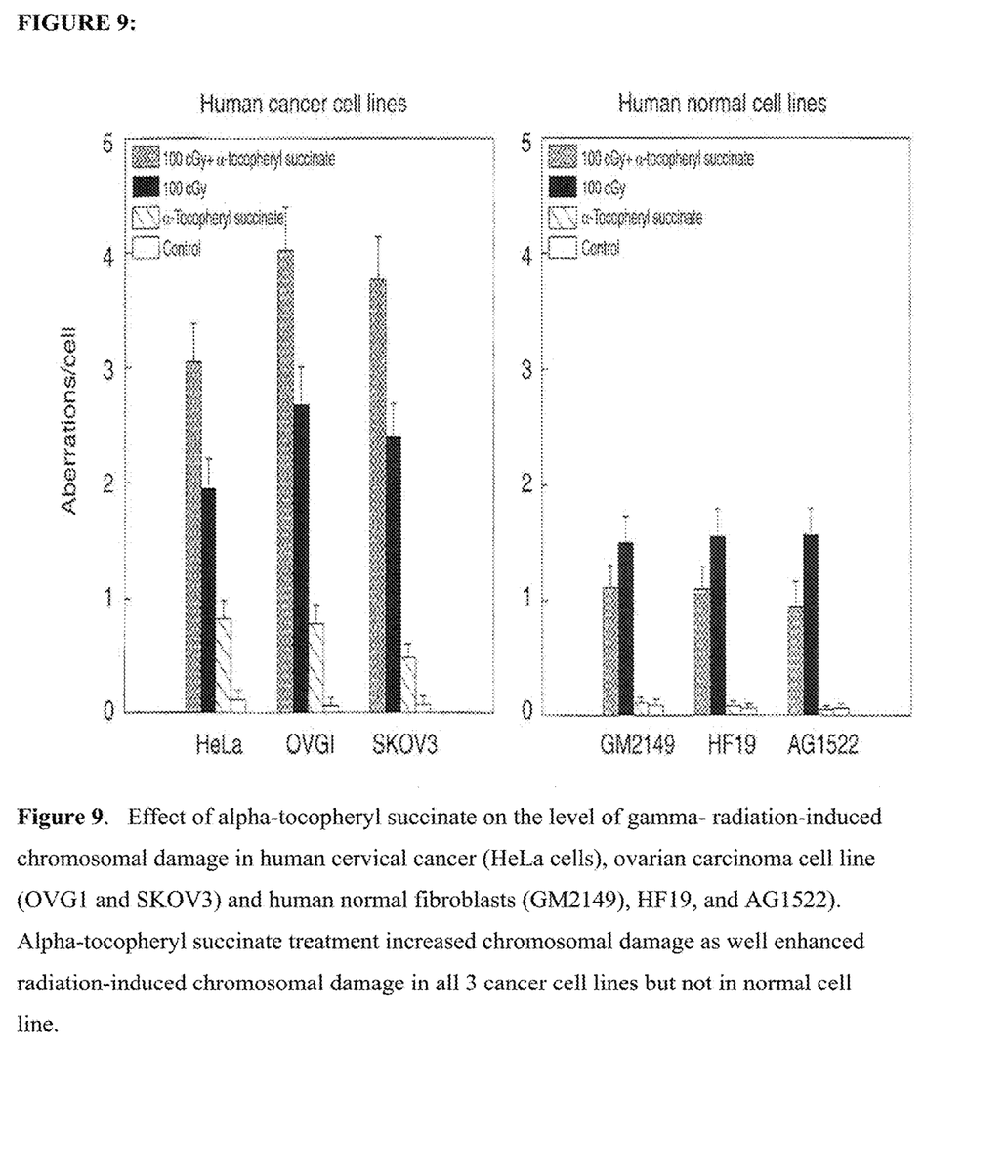
FIG. 9 shows effect of alpha-tocopheryl succinate on the level of gamma-radiation-induced damage in human cervical cancers.
Figure 11:
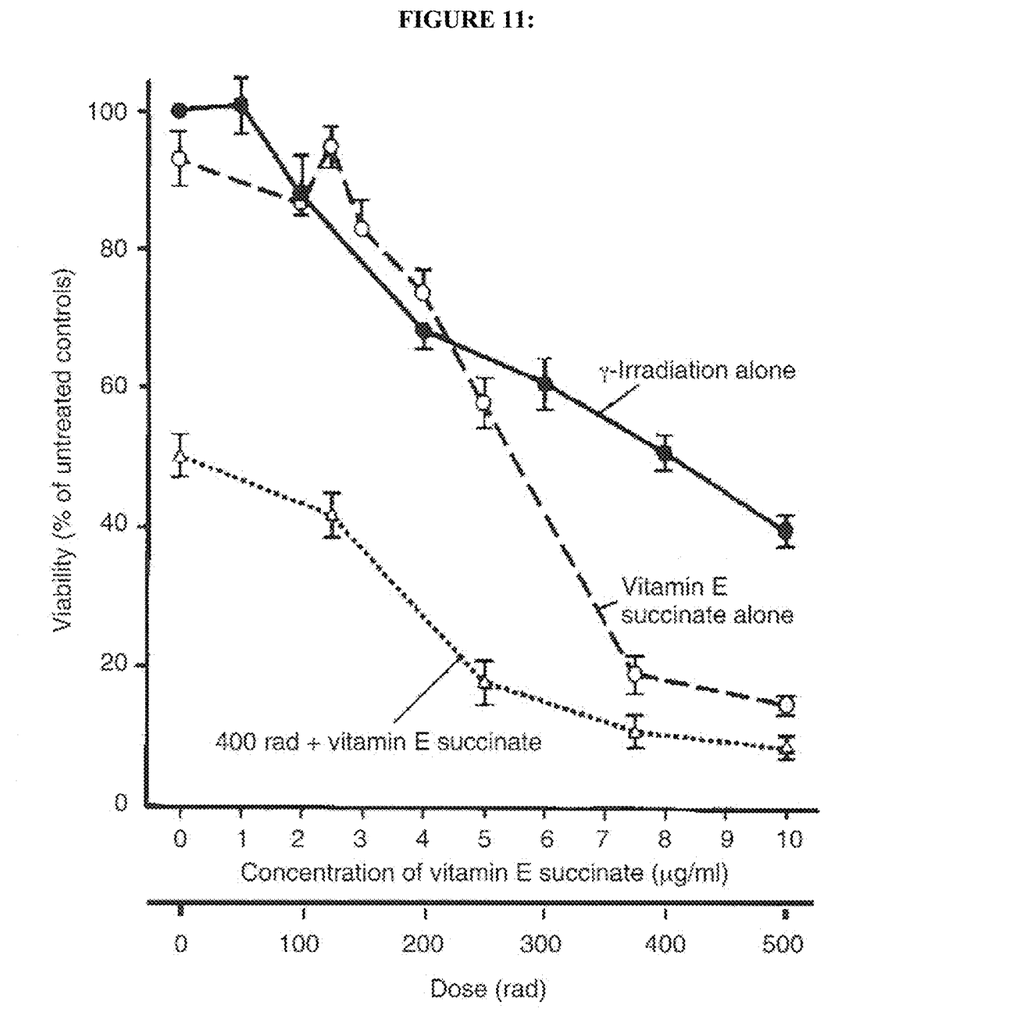
FIG. 11 shows effects of neuroblastoma cells that were irradiated and given Vitamin E succinate.

Vitamin E: D-alpha-tocopheryl succinate (vitamin E succinate) treatment at growth inhibitory doses before irradiation enhanced the cytotoxic effects of gamma-irradiation on murine neuroblastoma cells in culture (FIG. 11). Vitamin E succinate induced chromosomal damage in human cervical cancer cells and ovarian cancer cells, but not in human normal fibroblasts in culture. In addition, vitamin E succinate enhanced the levels of radiation-induced chromosomal damage in cancer cells, but it protected normal cells against such damage (FIG. 9). Vitamin E succinate at growth inhibitory doses enhanced the cytotoxic effects of adriamycin on human prostate cancer cells in culture. Vitamin E succinate also enhanced the toxicity of Adriamycin on human cervical cancer cells (HeLa cells) but not on human normal fibroblasts (Table 5 in FIG. 5).

Coenzyme Q10: Coenzyme Q10 at concentrations of 0.9 μM to 9.0 μM did not inhibit the growth of human breast cancer cells in culture and did not interfere with the cytotoxicity of doxorubicin. Treatment of rats with coenzyme Q10 (10 mg/Kg) prevented doxorubicin-induced cardiomyopathy by attenuating fibrosis and cell death. Preclinical and clinical studies suggest that coenzyme Q10 protected anthramycin-induced cardiomyopathy. On the other hand, another study showed that coenzyme Q10 treatment of human glioma cells in culture increased the sensitivity to ionizing radiation to DNA damage and apoptosis as well as enhanced the cytotoxicity of TMZ (temozolomide) without affecting non-transformed astrocytes.

Resveratrol: In breast cancer cells in culture (MCF-7), treatment with resveratrol at a dose of 10 μM before irradiation increased apoptosis pathway leading to decrease the ratio of Bax/Bcl2 and increased activity of caspase 8 in 24 hours. Resveratrol treatment also increased the expression of p53 and blocked tumor cells in S-phase of the cell cycle. Thus resveratrol acts as a radiosensitizing agent in breast cancer cells.

In NK/T cell lymphoma (NKTCL) derived from a highly aggressive non-Hodgkin lymphoma with poor diagnosis, resveratrol treatment reduced cell proliferation and cell cycle arrest in S phase in a dose-dependent manner. This treatment induced apoptosis through mitochondrial pathway by downregulating MCI-1 (myloid cell leukemia-1) and survivin proteins, upregulating the levels of BaxX (Bcl2 associated X) and Bad (BCl2 associated agonist of cell death) that regulate apoptosis, and activate of caspase-3 and caspase-9, which kill cancer cells. In addition, resveratrol treatment inhibited phosphorylation of AKT (also called protein kinase B) and Statt3 (signal transducer and activator of transcription 3) that regulate gene expression in the nucleus and mitochondrial function in tumor cells. It also activated DNA damage response (DDR) pathway in an ATM (also called protein kinase B), Chk2 (crystal structure of checkpoint kinase-2) and p53 (a tumor suppressor protein) dependent manner. Resveratrol in combination with ionizing radiation induced apoptosis in cancer cells by activating DDR. These results suggest that resveratrol treatment of lymphoma cells can bypass its protective pathways and mediate its growth-inhibitory effects by activating apoptosis pathways and by inhibiting anti-apoptosis pathways.

Resveratrol at doses of 2.5-10 μM inhibited the growth of androgen-sensitive (22RV1) and androgen insensitive prostate cancer cells but not of normal prostate epithelial cells. This treatment also enhanced ionizing radiation-induced apoptosis, -cell cycle arrest at G1-S phase of the cell cycle, and -double-strand DNA breaks on prostate cancer cells. Resveratrol treatment also increased radiation-induced activation of ATM and AMPK but inhibited basal and radiation-induced phosphorylation of AKT.

Curcumin: Although curcumin has been shown to exhibit antioxidant and anti-inflammation activities in preclinical studies, pre-treatment enhanced ionizing radiation-induced apoptosis in radioresistant cervical cancer cells by increasing the production of ROS and overactivation of mitogen-activated protein kinase1/2 (MEK1/2) pathway. Co-treatment of curcumin with arsenic oxide, an anti-leukemic drug or with lonidamine, a mitochondrial-targeting drug, increased the levels of apoptosis induced by these drugs but no similar effect was found with cisplatin on chronic myel-ogenous leukemia cells in culture. These combined effects of curcumin and cancer drugs on apoptosis were related to an increased release of cytochrome C and production of excessive amounts of ROS.

Figure 4:
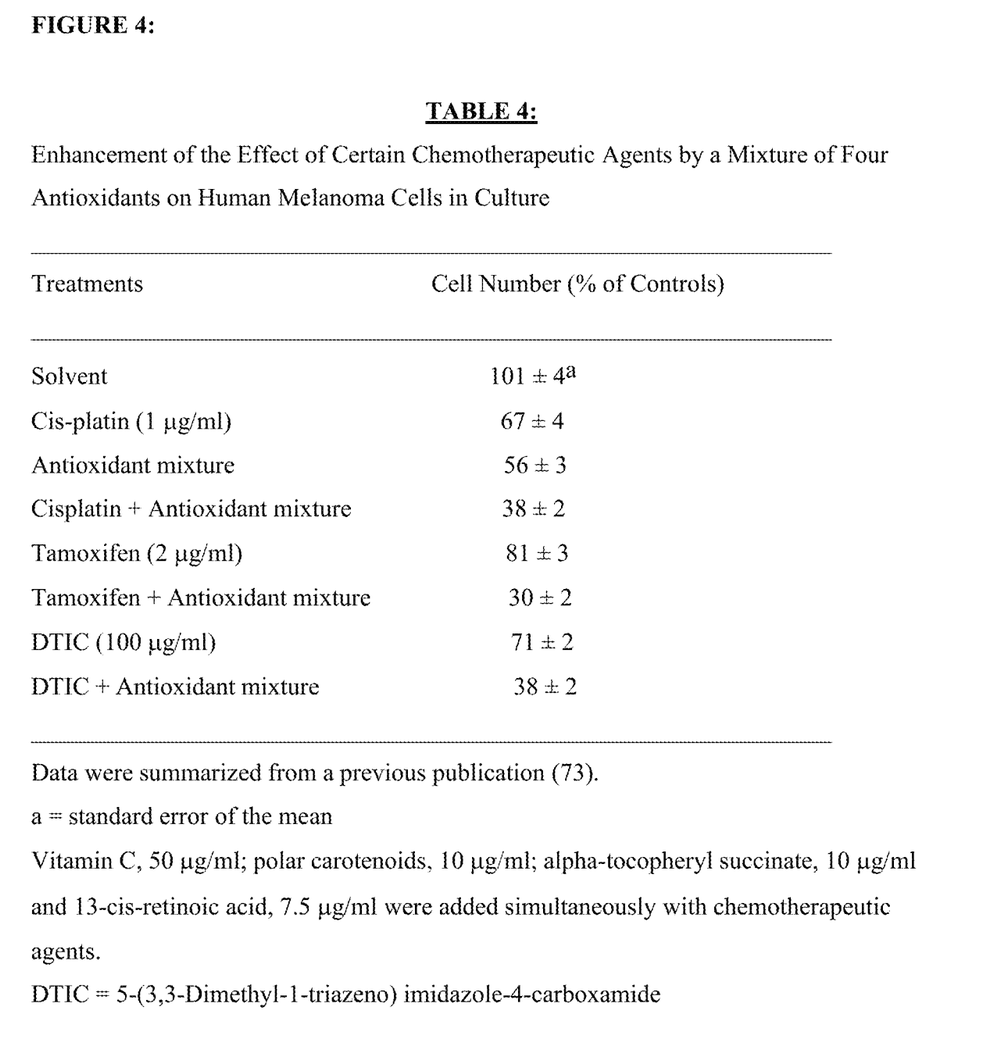
FIG. 4 shows a table with the effects of the interaction between chemotherapeutic agents and antioxidants human melanoma cells.

A mixture of retinoic acid, vitamin C, vitamin E succinate, and polar carotenoids reduced the growth of human melanoma cells (SK-30) in culture, and enhanced the cytotoxic effects of tamoxifen, cisplatin, and DTIC (Table 4 in FIG. 4).

High Doses of Antioxidants Enhance the Apoptotic Effects of Hyperthermia

Figure 6:
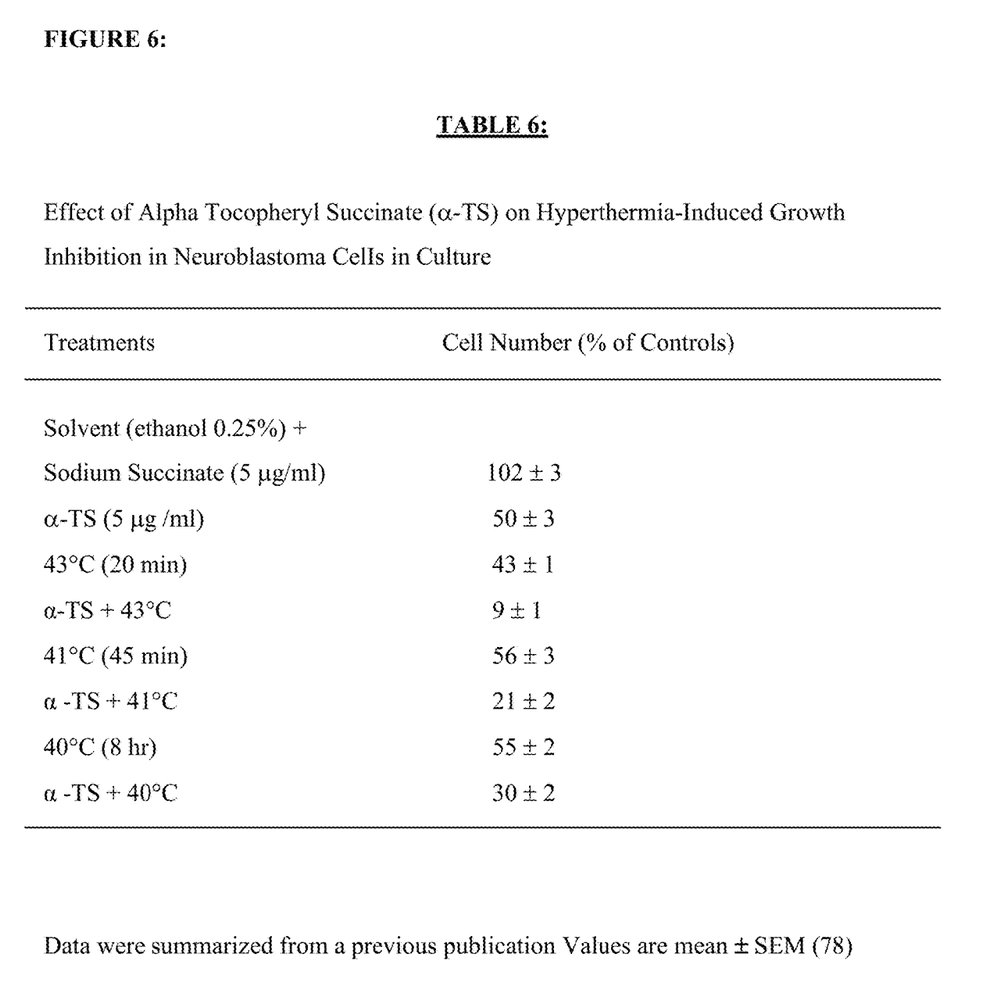
FIG. 6 shows a table with the effect of alpha tocopheryl succinate on neuroblastoma cells.

Hyperthermia at 40° 43° C. alone or in combination with radiation therapy is primarily used in the management of local tumor control after all standard therapeutic modalities have failed. Variable improvements in transient local tumor control have been observed. Vitamin E succinate treatment induced apoptosis and enhanced apoptotic effects of hyperthermia (40° C., 41° C., and 43° C.) in neuroblastoma cells in culture (Table 6 in FIG. 6). There are no other published studies on high-dose antioxidant on hyperthermia-induced apoptosis in cancer cells.

The question arises as to why high-dose antioxidants reduce the growth and induce apoptosis in cancer cells but not in normal cells. Are there one or more nutrients that are required by cancer cells for their survival and growth? Analysis of published studies suggests that increased uptake of glucose and uptake and metabolism of glutamine is absolutely necessary for maintaining bioenergetics and biosynthesis pathways for proliferation and growth of cancer cells. High-dose antioxidants inhibit glucose uptake and glutamine metabolism leading to the death of cancer cells. These studies are described here.

Glucose and Glutamine Requirements for the Survival and Growth of Cancer Cells

Glucose: The concept on metabolism of glucoses and glutamine described here is based on the analysis of several studies and reviews some of which are described here. Glucose and glutamine are most abundant nutrients in the plasma. Glucose is primarily needed to activate bio-energetic pathways, while glutamine is utilized to activate both bio-energetic and biosynthetic pathways in order to maintain proliferation of normal as well as cancer cells. However, Glucose metabolism in cancer cells is different from those of normal cells. For example, cancer cells use pyruvate kinase M2 to convert glucose to pyruvate that is converted to lactic acid by lactate dehydrogenase in the cytoplasm. During this processes 2 ATP per glucose molecule are produced. This process of generating energy is referred to as Warburg-Effect. This amount of energy is not enough for maintaining the proliferation and growth of cancer cells; therefore, they consume glucose at a much higher rate to generate sufficient energy for their survival and growth. In contrast to cancer cells, normal cells utilize pyruvate kinase M1 to convert glucose to pyruvate, which enters the mitochondria where oxidative phosphorylation processes generate 36 ATP per glucose molecule. Thus normal cells do not require as much glucose as cancer cells to meet their energy requirements. Excess glucose is converted to more lactic acid making cellular environment acidic. High glucose increased proliferation as well as ROS levels but it reduced phosphorylation of JNK (c-jun-N-terminal kinase) belonging to mitogen activated protein kinase in pancreatic tumor cells in culture, suggesting that these cancer cells require more glucose for continued proliferation and survival.

Glutamine: The study on the effects of nutrients on cancer cells in culture suggested that cancer cells are addicted to glutamine. A few reviews have analyzed the function of glutamine in cancer cells. Glutamine is utilized by cancer cells for continued proliferation and survival under the condition of metabolic stress. It provides source of energy, protein synthesis and nitrogen for nucleic acid synthesis. Glutamine is converted to glutamate by glutaminase 1 (GLS1) and then glutamate is converted to alpha-ketoglutarate, which enters into the TCA (tricarboxylic acid) cycle for generating energy.

While autophagy suppresses initiation of tumorigenesis in normal cells by eliminating damaged proteins and organelles, it provides substrates for growth and survival of cancer cells. Glutamine also inhibits autophagy by activating mechanistic target of rapamycin complex (mTORC). Excessive amounts of ROS are generated by mitochondria electron transport chain during progression of cancer that could kill cancer cells, however, glutamine derived glutathione provided protection against oxidative damage and thereby cancer cell continue to grow and survive.

The patients with oral cancer (stage III-6, stage IV-42) had elevated levels of MDA and reduced levels of antioxidant enzymes in lymphocytes, neutrophils, and serum compared to age- and gender-matched normal subjects. These biochemical changes can be restored to some extent by dietary supplementation with glutammune (66.66% L-glutamine). This study suggests that the patients with advanced oral cancer had a high oxidative environment that is needed for continued proliferation. This study did not measure the effect of glutamine on tumor growth following partial restoration of oxidative stress.

Lactate stimulates glutaminolysis and increases the uptake of glutamine in oxygenated cancer cells. It also induces HIF 1 (hypoxic inducible factor 1) that enhances the expression of c-myc, an oncogene, which plays a role in maintaining proliferation of cancer. Lung tumor cells take lactate from blood stream and convert to pyruvate, which enters the TCA for generating energy. Oxygenated cancer cells use lactate for oxidative metabolites instead of glucose, which then becomes available through blood vessels to hypoxic cells for glycolysis.

Cancer cells require increased levels of ROS during progression and metastasis of the disease. Glutamine catabolism leads to production of glutathione, which protects cancer cells from oxidative damage. Glutamine activates mTORC (mechanistic target of rapamycin complex) which regulates cancer cells proliferation and growth, most tumors have elevated levels of mTORC.

The studies discussed above suggest that glycolysis and glutaminolysis cooperate with each other in maintaining proliferation and growth of cancer cells. Inhibition of at any stage of glucose or glutamine metabolism may reduce the growth of cancer cells. Indeed, it has been shown that inhibition of glutamine metabolism enhances the sensitivity of Kras positive pancreatic ductal adenocarcinoma to radiation therapy by increasing oxidative stress. Since both glucose and glutamine are required for the growth of cancer cells it would be essential to interfere with their uptake or metabolism at the same time in order to reduce the survival of cancer cells. Some studies suggest that high-dose antioxidants appear to block the uptake of glucose and metabolism of glutamine in cancer cells. These studies are briefly described here.

High-Dose Antioxidants Inhibit of Glucose Uptake in Cancer Cells

Antioxidants inhibit the uptake of glucose in cancer cells. Some examples are described here.

Vitamin C: Vitamin C inhibited glycolysis by inactivating glyceraldehyde 3-phosphate dehydrogenase (GAPDH) and killed selectively human colorectal cancer (CRC cell line) carrying Kras mutation or Braf mutation. Because of these mutations, cancer cells become resistant to standard therapies. Since GAPDH is an important enzyme for energy metabolism and the production of ATP and pyruvate through anaerobic glycolysis in the cytoplasm, vitamin C-induced inactivation of this enzyme would create energy crisis in the tumor cells leading to cell death.

Alpha-lipoic acid: Alpha-lipoic acid at high doses reduced glucose uptake and reduced the growth of neuroblastoma cells and breast cancer cells in culture and in mice with transplanted breast cancer.

Quercetin and epigallocatechin gallate (EGCG): Quercetin blocked the uptake of glucose leading to inhibition of glycolysis and prevented the migration of breast cancer cells in culture by decreasing the levels of its marker matrix metalloproteinase 2 (MMP-2), MMP-9, and vascular endothelial growth factor (VEGF). This study also showed that quercetin also inhibited tumor growth and metastasis by inhibiting glycolysis in vivo. Both quercetin and EGCG inhibited the uptake of glucose and reduced the growth of estrogen receptor (ER)-positive (MCF7) and ER-negative MDA-MB-231 breast cancer cells in culture.

Resveratrol: Resveratrol-loaded polymeric nanoparticles reduced glucose metabolism and inhibited the growth of colon cancer cells in culture (CT26 cell line) and in CT26 transplanted mice. Resveratrol induced apoptosis in ovarian cancer cells in culture by inhibiting the uptake of glucose.

High-Dose Antioxidants Inhibit Glutamine Uptake and Metabolism

Antioxidants inhibit glutamine metabolism in cancer cells. Some examples are described here.

Resveratrol: Resveratrol and cisplatin treatment individually enhanced the levels of phosphorylated H2AX (yH2AX), a marker of DNA double-strand breaks, in hepatoma cells in culture, the combination of two produced more pronounced effects on the levels of yH2AX. Resveratrol treatment inhibited glutamine metabolism that accounted for the enhancement of growth inhibitory effects of cisplatin on hepatoma cells.

Vitamin D3: Treatment of H-ras transformed human breast epithelial cells with vitamin D3 inhibited glutamine uptake and reduced their growth. This effect of Vitamin D3 was mediated by reducing the level of a major glutamine transporter protein (SLC1A5).

Omega-3-fatty acids: Treatment of breast cancer cells in culture or mice carrying breast cancer cells inhibited glucose and glutamine metabolism, and reduced their growth. The combination of omega-3-fatty acids and rapamycin produced synergistic effects on cell cycle arrest and apoptosis and more pronounced inhibition in glutamine metabolism.

Experimental Therapy

Hyperthermia: Hyperthermia at 43° C. inhibited the growth of HCT-116 colon cancer cells by reducing the uptake of glucose.

High Doses of Antioxidants Bypass Protective Effects of High Expression of Nrf2 and Glutathione Peroxidase on Cancer Cells Nrf2, a nuclear transcriptional factor, is constitutively expressed in cancer cells. Activation of Nrf2 increases the level of antioxidant enzymes, which protect cancer cells from oxidative damage, allowing rapid progression and metastasis, and making them resistant to therapeutic agents. In addition, Glutathione peroxidase-2, which is highly expressed in cancer cells, produces enhanced level of glutathione that protects cancer cells from oxidative damage and make them resistant to therapeutic agents. High-dose antioxidants bypass the effect of these protective mechanisms by blocking glucose uptake and inhibiting glutamine metabolism.

Proposed Mixture of High Doses of Antioxidants for the Treatment of Cancer

Based on the studies presented in this manuscript, a mixture of high-dose antioxidants for increased reduction of tumor growth is proposed. This mixture contains high doses of vitamin A, vitamin C, vitamin D3, vitamin E succinate, R-a-lipoic acid, N-acetylcysteine, coenzyme Q10, curcumin, resveratrol, and natural beta-carotene, is suggested. In addition, the mixture contains all B-vitamins, and minerals selenium and zinc at the non-toxic levels. The proposed micronutrient mixture in combination with a standard or experimental therapy may enhance their effectiveness in reducing tumor growth more than produced by either agent alone, while causing no significant damage to normal cells.

Preparation of formulas: All high-dose antioxidants formulas are prepared in a powder form, which can be dissolved in water or Juice. The daily dose will be divided into three equal portions in three separate packages.

Dose schedule: Formula is orally administered to each cancer patient three times a day (morning, noon, and evening with a meal). Cancer patients who are to receive radiation therapy, chemotherapy or experimental therapy may start 7 days before starting the therapy, and continue for the entire treatment period. Formula should continue 7 days after completion of cancer therapy.

Type of cancer patients: High-dose antioxidant formula is recommended to all cancer patients irrespective of cancer type, who are schedule to receive radiation therapy, chemotherapy or experimental therapies.

High-dose antioxidant formula is also recommended for cancer patients who have become unresponsive to all therapies. If this formula reduces tumor growth, treatment can be continued with or without standard cancer therapy until the tumor disappears or patients become unresponsive to these therapies.

Numerous modifications and variations of the present invention are possible in light of the above teachings. It is therefore to be understood that within the scope of the attendant claims.

What is claimed is:

1. A composition comprising at least one antioxidant, at least one vitamin, at least one phytonutrient, and at least one mineral, wherein
   (a) said antioxidant is selected from the group consisting of R-alpha-lipoic acid, Coenzyme Q10, Vitamin A, Vitamin C, Vitamin E and combinations thereof,
   (b) said vitamin is selected from the group consisting of Vitamin D3, Vitamin B1, methylfolate Vitamin B2, Vitamin B3, Vitamin B5, Vitamin B6, Vitamin B9, Vitamin B12 and combinations thereof,
   (c) said phytonutrient is selected from the group consisting of curcumin, resveratrol, quercetin, and combinations thereof, and
   (d) said mineral is selected from the group consisting of selenomethionine, zinc glycinate and combinations thereof,
   wherein a therapeutically effective amount of said composition is intended to be administered to cancer patients in need thereof, and wherein said antioxidant, said vitamin, said phytonutrient and said mineral are the only therapeutically active agents in said composition.

2. The composition of claim 1 wherein the amount of said antioxidant in said composition is from about 15 to about 20,000 mg.

3. The composition of claim 1 wherein the amount of said vitamin in said composition is from about 8 to about 1800 mg.

4. The composition of claim 1 wherein the amount of said antioxidant in said composition is from about 800 to about 2,000 mg.

5. The composition of claim 1 wherein the amount of said antioxidant in said composition is from about 50 mcg to about 400 mcg.

6. The composition of claim 1 wherein the amount of said Vitamin A in said composition is from about 6,000 to about 25,000 IU.

7. The composition of claim 1 wherein said Vitamin A is retinyl palmitate.

8. The composition of claim 1 wherein the amount of said Vitamin C in said composition is from about 5,000 to about 20,000 mg.

9. The composition of claim 1 wherein said Vitamin C is calcium ascorbate.

10. The composition of claim 1 wherein the amount of said Vitamin D3 in said composition is from about 3,000 to about 12,000 IU.

11. The composition of claim 1 wherein said Vitamin D3 consist of cholecalciferol.

12. The composition of claim 1 wherein the amount of said Vitamin E in said composition is from about 1,000 to about 3,000 IU.

13. The composition of claim 2 wherein said Vitamin E is d-alpha-tocopheryl succinate.

14. The composition of claim 1 wherein the amount of said Vitamin B1 in said composition is from about 6 to about 12 mg.

15. The composition of claim 1 wherein said Vitamin B1 is thymine phosphate.

16. The composition of claim 1 wherein the amount of said Vitamin B2 in said composition is from about 6 to about 12 mg.

17. The composition of claim 1 wherein said Vitamin B2 is riboflavin.

18. The composition of claim 1 wherein the amount of said Vitamin B3 in said composition is from about 6 to about 18 mg.

19. The composition of claim 1 wherein said Vitamin B3 is nicotinamide riboside.

20. The composition of claim 1 wherein the amount of said Vitamin B5 in said composition is from about 6 to about 18 mg.

21. The composition of claim 1 wherein said Vitamin B5 is pantothenic acid.

22. The composition of claim 1 wherein the amount of said Vitamin B6 in said composition is from about 6 to about 18 mg.

23. The composition of claim 2 wherein said Vitamin B6 is pyridoxine chloride.

24. The composition of claim 1 wherein the amount of said Vitamin B9 in said composition is from about 400 to about 1,200 mcg.

25. The composition of claim 3 wherein said Vitamin B9 is methylfolate.

26. The composition of claim 1 wherein the amount of said Vitamin B12 in said composition is from about 8 mcg to about 50 mcg.

27. The composition of claim 1 wherein said Vitamin B12 is methylcobalamine.

28. The composition of claim 1 wherein the amount of said curcuminin in said composition is from about 800 to about 2,000 mg.

29. The composition of claim 1 wherein the amount of said resveratrol in said composition is from about 800 to about 2,000 mg.

30. The composition of claim 1 wherein the amount of said quercetin in said composition is from about 800 to about 2,000 mg.

31. The composition of claim 1 wherein the amount of said selenomethionine in said composition is from about 50 to about 300 mcg of selenomethionine.

32. The composition of claim 1 wherein the amount of said zinc glycinate in said composition is from about 10 to about 40 mg.

33. The composition of claim 1 wherein the amount of said R-alpha-lipoic acid in said composition is from about 800 to about 1,800 mg.

34. The composition of claim 1 wherein the amount of said Coenzyme Q10 in said composition is from about 800 to about 2,000 mg.

35. The composition of claim 1 wherein a therapeutically effective amount of the composition is intended to be administered to a cancer patient in need thereof on a daily basis.

36. The composition of claim 35 is wherein a composition is split into three equal parts, each of which is a therapeutically effective dose, and wherein each part may be administered to a cancer patient in need thereof three times per day.

37. The composition of claim 1 wherein a therapeutically effective amount of the composition may be administered with a meal.

38. The composition of claim 1 wherein a therapeutically effective amount of the composition may be administered to a cancer patient in need thereof for at least one week before standard cancer therapy.

39. The composition of claim 1 wherein a therapeutically effective amount of the composition is an oral dosage form.

40. The composition of claim 1 wherein a therapeutically effective amount of the composition may be administered to a patient in need thereof with or without cancer therapy.

41. The composition of claim 1 wherein said composition is in a form selected from the group consisting of powdered form, liquid form and a combination of powdered and liquid form.

* * * * *